United States Patent [19]
Jackson et al.

[11] Patent Number: 5,810,786
[45] Date of Patent: Sep. 22, 1998

[54] TISSUE-NUMBING ANESTHETIC ARTICLES

[75] Inventors: Richard R. Jackson, One Atlantic Ave., Swampscott, Mass. 01907; John N. Williams, Concord, Mass.

[73] Assignee: Richard R. Jackson, Swampscott, Mass.

[21] Appl. No.: 622,190

[22] Filed: Mar. 25, 1996

Related U.S. Application Data

[63] Continuation-in-part of PCT/US94/00492, Jan. 18, 1994, which is a continuation of Ser. No. 126,970, Sep. 24, 1993, Pat. No. 5,417,671.

[51] Int. Cl.$^6$ ........................................................ A61M 5/32
[52] U.S. Cl. ................................................................ 604/265
[58] Field of Search ............................ 604/265, 96–103, 604/111, 112, 209, 264, 280

[56] References Cited

U.S. PATENT DOCUMENTS

| | | |
|---|---|---|
| 3,576,760 | 4/1971 | Gould et al. . |
| 3,577,516 | 5/1971 | Gould et al. . |
| 3,610,247 | 10/1971 | Jackson . |
| 3,638,655 | 2/1972 | Doherty . |
| 3,832,252 | 8/1974 | Higuchi et al. . |
| 3,854,480 | 12/1974 | Zaffaroni . |
| 3,896,819 | 7/1975 | Zaffaroni et al. . |
| 3,948,254 | 4/1976 | Zaffaroni . |
| 3,978,203 | 8/1976 | Wise . |
| 4,164,560 | 8/1979 | Folkman et al. . |
| 4,421,333 | 12/1983 | Greco et al. . |
| 4,560,720 | 12/1985 | Adyogi et al. . |
| 4,581,028 | 4/1986 | Fox, Jr. et al. . |
| 4,591,496 | 5/1986 | Cohen et al. . |
| 4,612,337 | 9/1986 | Fox, Jr. et al. . |
| 4,806,621 | 2/1989 | Kohn et al. . |
| 4,867,968 | 9/1989 | Allen . |

(List continued on next page.)

FOREIGN PATENT DOCUMENTS

| | | |
|---|---|---|
| 0 377 477 A1 | 7/1990 | European Pat. Off. . |
| WO 95/08320 | 3/1995 | WIPO . |

OTHER PUBLICATIONS

Gebeieh, Charles, et al., *Polymeric Materials and Artificial Organs*; American Chemical Society, pp. 15–18, 1984.

(List continued on next page.)

*Primary Examiner*—Manuel Mendez
*Attorney, Agent, or Firm*—Fish & Richardson P.C.

[57] ABSTRACT

A drug delivery system comprising propathenone or lidocaine dissolved in thermoplastic resin is shown to be useful for prolonged release antiahrrythmia medications. More generally, a compound with topical anesthetic and plasticizing properties, or another drug having a similar structures containing an aromatic ring, is dissolved in polymeric material. Extrusion, co-extrusion, coating and diffusion techniques to form orally digestible granules, fibers, films and tubes such as endotracheal tubes, drainage tubes and other medical devices with the material containing drug are disclosed. Diffusion techniques in which the drug diffuses into the thermoplastic is also disclosed. A hydrophobic anesthetic or similar compound such as the base form of lidocaine or propathenone is used which is more soluble in the polymeric material than in water. Prilocaine base and dibucaine base are also used in examples. A water soluble form of the drug, achievable by reacting the base form of the drug dissolved in the polymer, is provided, e.g. at an exposed surface, to enable rapid onset of anesthesia or dosage. Balloons, films and extruded cross sections are shown. Barrier and metering layers control the direction and rate of application of the anesthetic or drug.

Compresses and wound dressings containing thermoplastic constituents in which a drug is dissolved provide prolonged administration of anesthetics and other drugs. An ointment or other fluid containing an ionic surfactant assists the transfer of the drug from the thermoplastic to the body.

44 Claims, 6 Drawing Sheets

U.S. PATENT DOCUMENTS

| | | |
|---|---|---|
| 4,879,135 | 11/1989 | Greco et al. . |
| 4,883,666 | 11/1989 | Sabel et al. . |
| 4,898,591 | 2/1990 | Jang et al. . |
| 4,917,686 | 4/1990 | Bayston et al. . |
| 4,977,894 | 12/1990 | Davies . |
| 4,994,047 | 2/1991 | Walker et al. . |
| 4,997,440 | 3/1991 | Dumican . |
| 5,279,594 | 1/1994 | Jackson . |
| 5,330,452 | 7/1994 | Zook . |
| 5,417,671 | 5/1995 | Jackson . |
| 5,478,567 | 12/1995 | Nakagawa et al. . |

OTHER PUBLICATIONS

Bruck, Stephen, *Blood Compatible Synthetic Polymers*; Charles C. Thomas, pp. 23–24, 1974.

*American Heritage Dictionary*, 2nd edition, 1982. pp. 106, 108, 442, 1262.

*The Merck Index*, ninth edition, 1976, pp. 3001 and 5331.

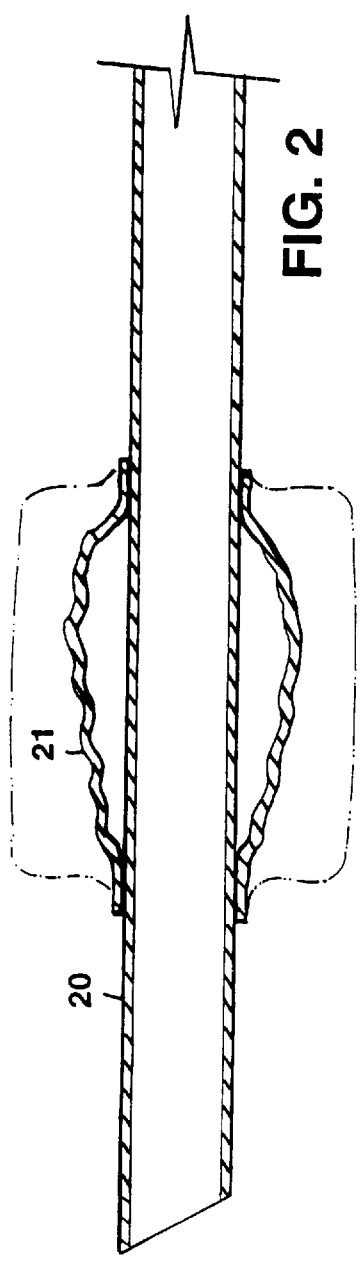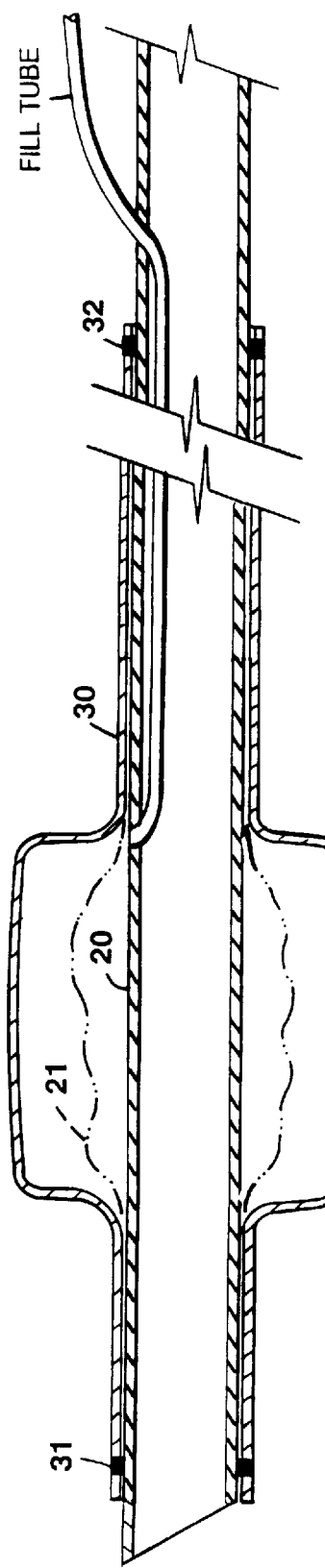

> Introduce as feed stock to an extruder or other plastics-forming system a polymer in which selected anesthetic base is soluble, and a plasticizer which comprises at least in part a topical anesthetic in base form.

> Extruding or otherwise forming the feed stock under conditions in which the anesthetic base is in solution in the polymer at least during one stage of manufacture and forming a product having a surface through which the anesthetic is administered.

FIG. 11

> Preform a medical device, or surface layer of it, of polymer material in which selected anesthetic base is soluble, the substance of the preformed device or layer having less plasticity than the desired final characteristic.

> Applying soluble anesthetic base under conditions to cause anesthetic base to enter into solution into the polymer material and reach a surface-accessible state, the anesthetic tube base contributing plasticity to achieve the desired final characteristic.

FIG. 12

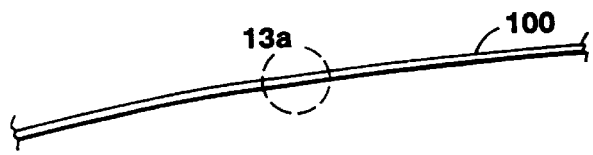
FIG. 13
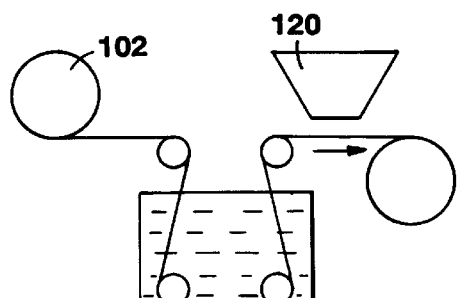
FIG. 18
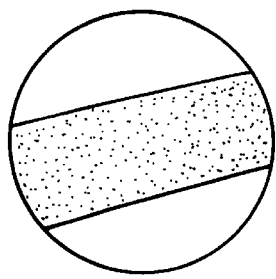
FIG. 13a
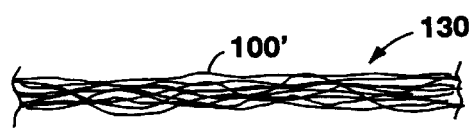
FIG. 19
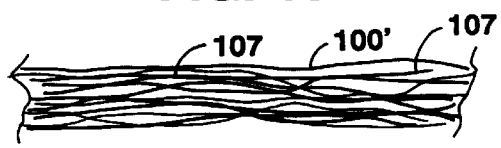
FIG. 20
FIG. 17
FIG. 14
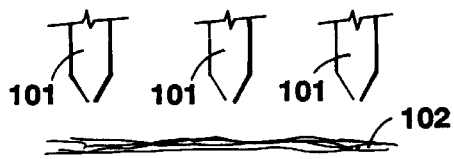
FIG. 15
FIG. 16
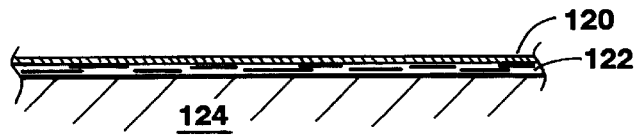
FIG. 21

TISSUE-NUMBING ANESTHETIC ARTICLES

SUMMARY OF THE INVENTION

This application is a continuation-in-part of International Application No. PCT/US94/00492 with international filing date of Jan. 18, 1994, which was a continuation of U.S. application Ser. No.: 08/126,970 filed Sep. 24, 1993, issued on May 23, 1995 as U.S. Pat. No. 5,417,671.

The invention relates to drug compositions and delivery systems, and the methods of their manufacture and use.

In one respect, the invention relates to compositions and methods for specifically enabling release of the drug propafenone or lidocaine, administered as an antiarrhythmic.

The invention also relates to drug delivery systems for delivering propafenone or lidocaine to the body over prolonged periods for other therapies.

In another aspect the invention relates more generally to compositions and methods that enable gradual or prolonged release of drugs to the body. This aspect especially concerns drugs having local or topical anesthetic properties and to drugs that have molecular structure similar to drugs that have such properties.

The invention also relates to anesthetizing and drug delivery systems useful at surgical sites for prolonged administration of drugs.

The invention also relates to intubation devices which are introduced into body passages of human and non-human animals in certain medical procedures. More generally, it relates to medical devices that have a local anesthetizing effect and to methods of their manufacture.

Patients who have undergone surgery often suffer pain and discomfort at the surgical site. The invention relates to relieving such pain and discomfort without generally sedating the patient.

When conventional intubation devices are introduced into body passages in connection with medical procedures they cause discomfort and often elicit ejection reactions such as coughing or gagging by the patient which interfere with the procedure and may be injurious to the patient. An object of the invention is to provide in an intubation device a tube which dispenses a topical anesthetic to contiguous tissue in the body passage to reduce or eliminate the discomfort and undesired reactions.

In accordance with one aspect of the invention, I have discovered that drugs having at least one aromatic ring (e.g., at least one substituted or unsubstituted benzene ring), and melting point in the range of processable thermoplastic resins, with the drug in base form (e.g., includes at least one free amide or amine hydrogen in its structure), can be dissolved in effective concentrations in thermoplastic resin. For many conventional low or medium molecular weight resins having processing temperatures between about 250° F. and 350° F., numerous of the drugs have been found to be soluble at useful levels. For high molecular weight resins, with processing temperatures up to about 450° Fi, additional drugs may be dissolved at useful levels.

The drug is present at the surface of the resin or will diffuse to the surface of the resin, where it can treat contacted tissue or enter body fluids or fluids associated with the body. In certain instances, the drug in base form, after being dissolved in the resin, is converted with acid to salt form soluble in body fluids. This is done as a further step during manufacture of the composition, or prior to administration, or during residence in the body. In many instances, in addition to the drug being present in a superficial resin layer in either base or converted salt form, the drug is also present in base form at deeper levels in the resin from which it gradually diffuses to the surface to provide a prolonged effect. This feature can be employed with the drug dissolved in orally administratable granules of coarse or fine powders of the thermoplastic resin, in a coating or surface layer or the main body of a functional object comprised of resin, or in sheets or fibers or films of resin.

Certain preferred embodiments of these aspects of the invention, and of other aspects described below, have one or more of the following features.

In certain embodiments the drug has a single benzene ring; the drug of base form is soluble in resins or polymers in which phthalates, glycolates, or citrates are soluble; the drug has local anesthetic properties (whether or not it is generally used as a local anesthetic); the drug is an antiarrhythmia or antiseizure drug having local anesthetic properties; the antiarrhythmia drug is propafenone or lidocaine; the drug is a local or topical anesthetic medication; the drug is an adrenergic blocking drug such as atenol; the drug is a sympathomimetic drug such as pseudoephedrine, terbutaline or phenylpropanolamine; the drug is an analgesic or antipyretic such as acetaminophen, phenacetin or ibuprofen; the drug is a stimulant of the nervous system, e.g. a psychostimulant such as methylphenidate.

Also, the drug is soluble in polymers or copolymers of resins selected from polyvinyl chloride, chlorinated polyethylene, cellulose nitrate, ethyl cellulose, cellulose acetate, polystyrene, polyvinyl butyryl, acrylic resins, alkyl alkylacrylate resins (e.g., methyl methacrylate, ethyl ethacrylate, or other lower alkyl acrylates), acrylonitrile rubbers, and chlorinated rubbers (e.g., neoprene); the drug is formulated as resin granules such as fine or coarse powder in tablet or capsule form suitable for oral administration; the resin is in orally administratable form, and has characteristics whereby the drug is released in the stomach and/or in the lower portion of the gastrointestinal system after which the resin is eliminated through the bowel; the resin resides for prolonged periods in contact with tissue or body fluid; the resin is formed as an implant; the resin is formed to lie adjacent a surgical or trauma site to administer anesthetic or other medication to the site; the resin is in the form of a thin, flexible wall or fiber of polymeric resin exposed to contact tissue; the resin is configured to deliver local or topical anesthetic in the region of an incision or wound; the resin is configured to perform an added function; the resin is configured to perform the added function of a fluid-conducting tube; the resin is configured to serve as a feeding tube; the resin is configured to serve as a drainage tube; the resin is configured as an irrigation or fluid drug administration tube; the resin is configured to form a functional bandage or compress; the resin is loaded with (has dissolved within it) a plurality of drugs, wherein the plurality includes drugs that have the same or different properties.

Another aspect of the invention is a wound or incision-contacting device formed to reside at a surgical point, and formed at least in part of thermoplastic resin in which a topical anesthetic or other drug is dissolved according to the invention. Such a device can reduce local pain and discomfort and promote healing.

Certain preferred embodiments of the wound or incision-contacting device have one or more of the following features.

The device includes a drug in base form dissolved in resin and in water soluble salt form associated with the resin. The salt form is a hydrochloride salt. The device includes hydrophilic resin in which the base form is dissolved and in which the salt form is imbibed in aqueous solution or is in the form of crystal deposits that result from inbibing and subsequent drying. The device is a tube having a surface that contacts tissue to be treated. The device is a film having a surface that contacts tissue to be treated. The device is present in a compress or bandage. The device is formed at least in part of thermoplastic fibers in which the drug is present. The device is a suture formed at least in part of thermoplastic resin in which the drug is dissolved. The fibers are at least part of a textile material. The material is a non-woven. The fibers are hydrophobic. Hydrophobic fibers are combined with hydrophilic fibers that contain an aqueous substance that promotes release and transport of the drug from the hydrophobic resin. The device is combined with a fluid or ointment that promotes transport of the drug. The fluid or ointment contains a drug, and the drug from the resin is effective to replenish the drug in the fluid or ointment. The drug in the fluid or ointment and the drug dissolved in the resin include topical anesthetics. The fluid or ointment includes an ionic surfactant that promotes diffusion of the drug through tissue. The fluid or ointment includes a thickener. The fluid or ointment includes carboxypoly methylene (Carbopol™). The fluid or ointment that cooperates with the drug dissolved in the resin includes a combination of topical anesthetics and an emulsifier such as Tween™ (a polyoxyethylene fatty acid ester). The combined anesthetics in the fluid or ointment are prilocaine and lidocaine.

Another aspect of the invention is a wound or incision treating device comprising fibers of hydrophobic resin in which a drug, and especially an anesthetic base, is dissolved.

Another aspect of the invention is a wound or incision treating device comprising fibers of hydrophilic resin in which a salt form of anesthetic is imbibed or deposited as crystals.

Certain preferred embodiments of these aspects have one or more of the following features. The device comprises a combination of fibers of hydrophobic and hydrophilic resin. The fibers of both types of resin carry a drug. An aqueous solution in the hydrophilic fibers is adapted to assist in transport or migration of base-form drug dissolved in the hydrophobic resin. The aqueous solution in the hydrophilic fibers is acidic and adapted to convert the base form of the drug to a water soluble salt.

In accordance with another aspect of the invention, I have discovered that topical anesthetics in base form, in their own right, are potent, soluble plasticizers for polyvinyl and similar resins, and in fact, are useful as a substitute for part of the necessary plasticizer or even by themselves without the addition of other plasticizers, to produce flexible medical devices that have desired local anesthetizing effect.

According to another aspect of the invention, such a topical anesthetic with plasticizer properties is incorporated in the polymeric material making up the wall of a tube or other medical device in appropriate balance with any other plasticizer being employed to produce a product having desirable flexible properties and shelf life.

In certain preferred embodiments the anesthetic is present in solution throughout the wall thickness of the tube or device, while in other instances it is present in solution in a flexible layer or coating on the device. In the latter case, a barrier or other provision may deter diffusion of the anesthetic into the underlying body.

While the tube, for instance, is in place within a body passage, the anesthetic compound diffuses to the surface of body tissue touched by the tube where its anesthetic effect suppresses discomfort and undesired rejection reactions. The base form of anesthetic compound employed according to the invention is hydrophobic, which is more soluble in the polymeric wall material of the tube than in water. Because of the hydrophobic properties, a quantity of anesthetic compound can be stored in solution in the polymeric wall material of the tube and this stored anesthetic compound is not washed out by the aqueous fluid which is present in the body passage. As a result, the anesthetic compound is transferred only to the contiguous tissue of the body passage and not disseminated systemically through the aqueous fluids. Since the anesthetic compound is thus dispensed only to the contiguous tissue of the body passage, the quantity of anesthetic compound stored in the tube wall is sufficient to maintain effective anesthesia of the body passage for hours or days, and undesired effects of a general dissemination through the body are avoided.

Advantage of the invention however can also be taken in cases where the water-soluble form of the anesthetic is desired, e.g. for rapid dissemination from the outer surface of the tube. In this case the base form of the anesthetic, e.g. lidocaine, is initially dissolved in the vinyl of a tube or a coating on the tube to achieve uniform distribution, and subsequently a post treatment with e.g. hydrochloric acid, is employed to convert the anesthetic, e.g. all of it or a part of it nearest the surface, to the water soluble hydrochloride form, which is capable of being rapidly mobilized upon contact with body fluids.

In one particular aspect, the invention features a tube for introduction into a body passage of an animal for medical purposes. The inner surface of the tube has a wall which defines an interior lumen, while the outward facing surface of the wall contacts the body tissue of an animal upon placement of the tube in a body passage of the animal. Dissolved into the polymeric wall material of the tube is a topical anesthetic compound which is more soluble in the wall material than in water and which is at an appropriate concentration, in balance with other constituents of the wall material, such that it contributes as plasticizer to render the wall material flexible to a predetermined desired degree while being in concentration such that diffusion of the compound to a surface of the body passage in contact with the tube is at a rate effective to maintain anesthesia.

Preferred embodiments have one or a number of additional features.

The topical anesthetic compound is unreactive with ethylene oxide as used in sterilizing procedures.

The wall of the tube is composed entirely of a single polymeric material which may be a polyvinyl chloride polymer or a vinyl-urethane copolymer.

The topical anesthetic dissolved in the polyvinyl chloride tube is lidocaine base or prilocaine base, though in certain instances dibucaine base or other anesthetics of this class or mixtures thereof can be employed; the topical anesthetic dissolved in the tube made of a vinyl-urethane copolymer may be similarly selected.

According to another aspect of the invention, a flexible tube for introduction into a body passage of an animal for medical purposes is provided, the tube having a wall with an inner surface defining an interior lumen, the wall having an outward facing surface which, when the tube is emplaced in a body passage of an animal, contacts body tissue of the animal, the wall of the tube being composed of wall material having dissolved therein a topical anesthetic compound, the topical anesthetic compound being more soluble in the wall material than in water, the concentration of anesthetic compound in the wall material being such that it contributes as plasticizer to render the wall material flexible to a predetermined desired degree while being in concentration such that when the tube is emplaced in and in contact with an animal's body passage, anesthetic compound diffuses to a surface of the body passage in contact with the tube at a rate to be effective in maintaining anesthesia.

Preferred embodiments have one or a number of additional features as follows.

The tube is in the form of an endotracheal tube, to which an inflatable cuff is affixed, the inflatable cuff being comprised of a thin wall material having dissolved therein a topical anesthetic compound that is more soluble in the wall material than in water.

The tube is in a form placeable into the body through the nose, preferably the tube being a naso-gastric feeding tube.

The tube is in the form of a drainage tube having drainage entry holes along a portion of the tube, preferably the tube being constructed to lie in the posterior gutter along the spine.

The tube is constructed to pass through the abdominal wall, preferably the tube being constructed to cross the peritoneum and pass through the stomach wall.

The tube is a Foley catheter, preferably a balloon on the Foley catheter being comprised of a thin wall material having dissolved therein a topical anesthetic compound that is more soluble in the wall material than in water.

A superficial portion of topical anesthetic on the tube is of water-soluble form.

The tube is of extruded form produced by the process of extruding a feed stock comprising resin and topical anesthetic soluble in the resin.

The tube is produced by the process of applying the anesthetic to a surface of a preformed tube under conditions enabling the anesthetic to enter into solution in the wall material.

The wall material of this aspect of the invention and the other aspects that follow further preferably comprise polyvinyl chloride or vinyl-urethane copolymer, and the anesthetic compound is lidocaine base, dibucaine base, prilocaine base or combinations thereof. Also in the topical anesthetic compound is unreactive with ethylene oxide as used in sterilizing procedures.

According to another aspect of the invention a medical device for introduction into a body of an animal for medical purposes is provided, comprising a plasticizable resin, the resin having a predetermined desired quantity of plasticizer chosen to determine a predetermined flexibility characteristic for the resin, the plasticizer quantity being comprised of at least about 25% topical anesthetic base soluble in the resin, the topical anesthetic base being more soluble in the resin than in water, the concentration and character of the anesthetic in the resin being such that when the medical device is emplaced in and in contact with an animal's body fluid or tissue, anesthetic compound diffuses to a surface of the device and to the fluid or tissue in contact with the device at a rate to be effective to provide a desired dosage.

In preferred embodiments of this aspect, the medical device comprises a tube having a wall defining an interior lumen, the wall having an outward facing surface which, when the tube is emplaced in a body passage of an animal, contacts body tissue of the animal, the wall of the tube being comprised of wall material having dissolved therein the topical anesthetic base.

According to another aspect of the invention a medical device is provided in the form of an inflatable member comprising a thin, flexible wall of polymeric resin, at least an outer portion of the thin, flexible wall having dissolved in the resin a topical anesthetic base that is characterized by being more soluble in the resin than in water.

In preferred embodiments the inflatable member comprises a cuff for an endotracheal tube or is in the form of an inflatable sleeve extending along the length of a medical tube or is in the form of a balloon of a Foley catheter.

In certain preferred embodiments the thin wall is comprised of multiple layers as a result of being produced by co-extrusion of differing polymeric resin compositions, at least one of the layers having the anesthetic dissolved therein.

According to another aspect of the invention a medical device is provided having at least a portion of multiple layer form as a result of being produced by coextrusion of differing polymeric resin compositions, at least one of the layers having dissolved therein a topical anesthetic base that is characterized by being more soluble in the constituent resin than in water.

In preferred embodiments of this aspect of the invention a further layer on one side of the layer in which the anesthetic is dissolved is a barrier layer comprised of a polymeric resin in which the anesthetic base is not as soluble as it is in the layer in which the anesthetic is dissolved, in certain preferred embodiments the barrier layer being comprised of polyethylene.

According to another aspect of the invention a medical device is provided having at least a polymeric resin portion of extruded form as a result of extrusion of pellets of starting resin in which an anesthetic base is dissolved.

Another aspect of the invention is a medical device having at least a polymeric portion in which prilocaine base is dissolved as a result of application of prilocaine base in liquid form to a preformed polymeric portion under conditions enabling the prilocaine to enter into solution into the resin of the preformed portion.

In another aspect a medical device is provided having at least a polymeric portion containing a water-soluble anesthetic produced by the process of treating with a reactant the polymeric portion in which anesthetic base is in solution.

In preferred embodiments of this aspect the water-soluble anesthetic is disposed in the region of an exposed surface of the device and, deeper in the portion, anesthetic base is dissolved in the constituent resin. Preferably the water soluble form of anesthetic is a hydrochloride of the anesthetic.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, dissolving into the wall material of the tube an anesthetic compound that has topical anesthetic properties and that is more soluble in the wall material than in water, the quantity of the anesthetic compound dissolved into the wall material being such that the tube has the desired mechanical specifications and when the tube is emplaced in and in contact with an animal's body passage, anesthetic compound diffuses to a surface of the body passage in contact with the tube at a rate to be effective in maintaining anesthesia.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, preparing a transfer solution of an anesthetic compound that has topical anesthetic properties and that is more soluble in the wall material than in water in a volatile transfer fluid in which the anesthetic compound is soluble, applying the transfer solution to the outer surface of the tube to form a coating thereon containing anesthetic in sufficient quantity to provide to the tube desired mechanical specifications and anesthetizing effect, and evaporating from the coating the volatile transfer fluid.

According to another aspect of the invention a method is provided for making an anesthetizing tube for introduction into a body passage of an animal for medical purposes, comprising the steps of combining particles of an organic polymeric material and an anesthetic compound that has topical anesthetic properties and that is more soluble in the wall material than in water, the anesthetic being in sufficient quantity to provide to the tube desired mechanical specifications and anesthetizing effect, the combining step including heating the polymeric material to incorporate the anesthetic compound into the polymeric particles, to form anesthetic-infused polymeric material, and extruding the anesthetic-infused polymeric material to form a tube of dimensions suitable for introduction into a body passage of an animal for medical purposes.

According to another aspect of the invention, a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, placing the tube together with a quantity of an anesthetic compound that has topical anesthetic properties and that is more soluble in the wall material than in water in a common chamber, evacuating the chamber and maintaining the chamber at elevated temperature for sufficient time to effect transfer to and dissolution into the tube of the anesthetic compound, in sufficient quantity to provide to the tube desired mechanical specifications and anesthetizing effect.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, and coating the tube with an anesthetic liquid that includes prilocaine base anesthetic either by itself or in mixtures with lidocaine base under conditions enabling the prilocaine to dissolve into the wall of the tube.

According to another aspect of the invention a method is provided for making an anesthetizing tube for introduction into a body passage of an animal for medical purposes, comprising the steps of fabricating a tube having dimensional and mechanical specifications suitable for insertion into a body passage of an animal, the tube having a wall made of an organic polymeric wall material, with anesthetic dissolved in the wall of the tube and thereafter reacting at least a portion of the anesthetic lying near the surface to form a water-soluble form of the anesthetic near the surface.

Another aspect of the invention is a medical device for introduction into a body of an animal for medical purposes, comprising a plasticizable resin, the resin having a predetermined quantity of plasticizer chosen to determine a predetermined durometer characteristic, at least part of the plasticizer serving to attain the predetermined characteristic comprises at least one topical anesthetic compound that has plasticizer properties and is more soluble in the wall material than in water, the concentration of anesthetic compound in the wall material being such that when the medical device is emplaced in and in contact with an animal's body tissue or fluid, anesthetic compound diffuses to a surface of the device and into the tissue or fluid at a rate to be effective to provide a desired dosage.

Preferred embodiments of this aspect have one or more further features.

The plasticizer present comprises two or more plasticizers, one of which has the characteristic of enhancing the diffusion rate through the resin of the anesthetic compound.

The anesthetic base is lidocaine and at least 25% of the plasticizer is diisooctylpthalate.

At least 25% of the plasticizer present is topical anesthetic base.

Substantially all of the plasticizer is comprised of one or more topical anesthetic bases.

According to another aspect of the invention a method is provided of preparing an anesthetic article comprising providing a vinyl polymer in particle form such as pellets or power, imbibing into the polymer particles a plasticizer comprising an anesthetic base soluble in the polymer at relatively low temperature, forming the imbibed polymer into granules or the like at higher temperature, and extruding the granules or the like to form the anesthetic article.

Preferred embodiments of this aspect have one or more of the following features.

The plasticizer comprises at least 25% topical anesthetic base.

The plasticizer is a mixture of two or more plasticizers.

The mixture comprises lidocaine and diisooctylpthalate.

Substantially all of the plasticizer is one or more topical anesthetic bases.

The invention also provides a method of administering an anesthetic comprising disposing in a communicating relationship with body tissue or body fluid a vinyl polymer, wherein the anesthetic is of base form dissolved in the polymer.

A medical article is also provided, constructed to administer anesthetic within a body comprising a plasticizable resin, the resin containing a quantity of plasticizer, wherein a substantial part of the plasticizer is topical anesthetic base that contributes anesthetic to be administered by the article.

A plasticizable resin endotracheal tube shaft is provided, wherein the shaft comprises a topical anesthetic base dissolved in the resin.

A plasticizable resin endotracheal tube cuff is also provided, wherein the inflatable cuff comprises a topical anesthetic base dissolved in the resin.

The invention also provides a plasticizable resin endotracheal tube comprising a shaft and inflatable cuff, wherein the shaft and the inflatable cuff each comprises a topical anesthetic base and wherein the concentration of the topical anesthetic base in the exposed surface of the shaft is less than the concentration of the topical anesthetic base in the exposed surface of the cuff.

Also, the invention provides a device for introduction into a body passage of an animal for medical purposes, the device being at least partially covered with a relatively loose-fitting plasticizable resin film, wherein the film comprises a topical anesthetic base dissolved in the resin of the film.

Because of the discovered solubility and slow release of lidocaine base and the like in such resins as unplasticized PVC, it is realized that the combination can be used as a slow-release drug delivery system of lidocaine or the like to the body. For instance, with this system, lidocaine may be administered at dosages suitable as an antiarrythmia or antiseizure agent. Therefore, according to an aspect of the invention, a medical delivery system is provided comprising lidocaine base dissolved in a plastic resin in which it is soluble. In preferred embodiments of this aspect the plastic resin is polyvinyl chloride and in certain embodiments the plastic resin is in the form of orally administrable granules.

According to another aspect of the invention, an antiahrrythmic composition is provided comprising propafenone or lidocaine in effective quantity dissolved in polyvinyl chloride and an antiseizure composition is provided comprising lidocaine in effective quantity dissolved in polyvinyl chloride.

BRIEF DESCRIPTION OF THE DRAWINGS

FIG. 2 is a cross-section of an endotracheal tube with a shaft and inflatable cuff, the cuff shown deflated in solid lines.

FIG. 3 is a cross-section of an endotracheal tube with a film covering, the cuff shown inflated in solid lines.

FIG. 11 and 12 are process flow diagrams illustrating steps in preferred methods of manufacturing products according to the invention.

FIG. 13 illustrates a greatly magnified view of a fiber in which a drug is dissolved;

FIG. 13A diagrammatically illustrates a portion of the fiber magnified still more; while FIG. 14 illustrates a spinnerette for forming the fiber.

FIG. 15 and 16 illustrates the process of forming a non-woven using fibers according to FIG. 13.

FIG. 17 illustrates a bandage or compress formed of the non-woven of FIG. 14, while FIG. 18 shows a treatment of a non-woven.

FIG. 19 and 20 show the formation of sutures according to the invention.

FIG. 21 diagrammatically shows a compress according to the invention.

DETAILED DESCRIPTION OF PREFERRED EMBODIMENTS

Figure 1:
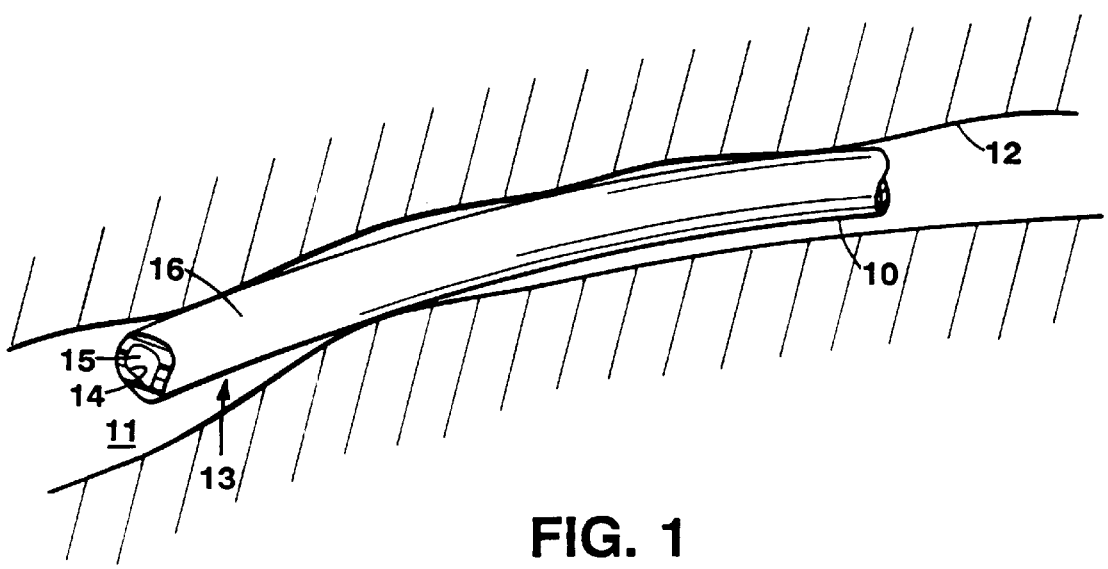
FIG. 1 shows a portion of a tube according to the invention emplaced in a body passage of an animal.
Figure 4:
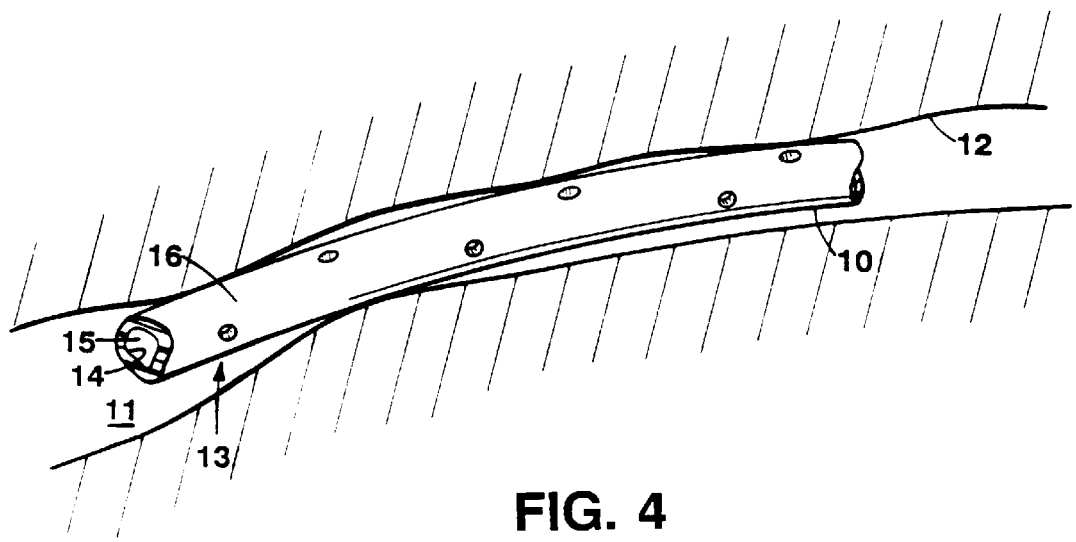
FIG. 4 is a cross-section of a drainage tube according to the invention.
Figure 5:
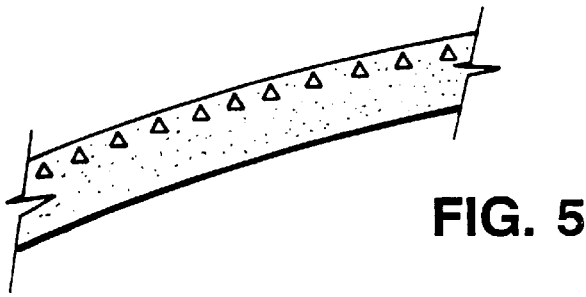
FIG. 5 is a diagrammatic partial cross-section of a further embodiment of the invention having a salt form anesthetic precipitate at an exposed surface.

As shown in FIG. 1, an intubation device including tube 10, according to the invention, is emplaced within body passage 11. Tube 10 has a wall 13 with an inner surface 14 defining lumen 15 and an outward facing surface 16 which contacts body tissue 12.

Wall 13 is composed of an organic polymeric wall material which may advantageously be polyvinyl chloride or vinyl-urethane copolymer. Dimensions of tube 10 are those conventionally used in intubation devices and may vary depending on the particular service of the device. A topical anesthetic compound is incorporated in the wall material of tube 10. The anesthetic compound is more soluble in the wall material of the tube than in water so that it will not be washed out of the wall material by aqueous fluids in the body passage. Anesthetic compounds having suitable solubilities are lidocaine base:
2(diethylamine)-N-(2,6-dimethyl-phenyl)acetamide, and dibucaine base:
2-Butoxy-N-[2-diethylamine)ethyl]-4-quinolinecarboxamide.

Lidocaine is the more soluble of the two in vinyl and is usually preferred. These anesthetics found to be effective as plasticizers, in particular lidocaine, can be incorporated in vinyl powder and passed through a heated screw extruder to produce pellets that may then be used in the conventional way as a plasticized feed material for producing a coating, film or an extruded shape.

Another local anesthetic base, prilocaine, can also be used. Though stated in the Merck manual that prilocaine needles melt at 37°–38° C., I have found that in practice, prilocaine base produced by reaction of the hydrochloride form with sodium hydrate (sodium hydroxide) is liquid at room temperature. This preparation also acts by itself as an excellent plasticizer e.g. of polyvinyl chloride. It can be incorporated into vinyl powder at a lower temperature (approximately 185° F.) than that used with the other materials mentioned above. The imbibed polymer preparation can then be used as feed material e.g. to make a very fine, soft and supple, film with lasting anesthetic properties, useful, e.g., as a cuff for an endotracheal tube or as a film covering for the shaft of an endotracheal tube or other catheter.

Prilocaine, or prilocaine with dissolved lidocaine base, e.g. a eutectic mixture of about 50% to 50% proportions, in particular, can also be employed in paint-like form by application to the surface of a pre-formed product. In this case the product or its surface layer are formed with reduced plasticizer content in anticipation of the plasticizing effect of the post-applied prilocaine.

These compounds are additionally advantageous in that they are not affected by conventional sterilization techniques which involve exposure to ethylene oxide.

The method of manufacture of tubes and other devices according to the invention is illustrated in the following examples.

EXAMPLE 1

A #16 urethral catheter made of polyvinyl chloride was placed in a large glass chamber together with 10 grams of lidocaine base. The lidocaine base was contained in a watch glass physically separated from the catheter. The glass chamber was evacuated to about 0.001 mm. Hg and placed in an oven maintained for 12 hours at 77 deg C. At the end of the 12 hour period the catheter was removed from the chamber and weighed. It had not changed in appearance, but had gained 550 mg. in weight. When the catheter was held against the tongue and lips, the area of contact developed marked numbness that became evident after 5 minutes and persisted for at least 15 minutes. The catheter was then sterilized in ethylene oxide sterilant, and aerated according to a standardized hospital procedure. After this it was inserted in a patient's urethra (with substantial discomfort) and taped in place. After about 3 minutes the discomfort abated markedly, and the catheter could be move about without problem. The catheter was left in place for eight hours without discomfort. There was no pain on removal or any unusual sequela.

EXAMPLE 2

A solution of 20% dibucaine base in food grade ethyl acetate was prepared. Fifteen #7 endotracheal tubes made of polyvinyl chloride were dipped in this solution to coat the outer surfaces with the solution. The coated tubes were than baked at 77 deg C. for 12 hours to drive off the ethyl acetate and dissolve the dibucaine base into the wall material of the tubes. The tubes were then sterilized with ethylene oxide, and aerated according to standard hospital practice. The tubes emerged from the process without any change in appearance. A tube thus treated when held against the tongue for 5 minutes produced a marked numbness on the contacted areas which lasted for 45 minutes. Ten of these tubes were introduced into the trachea (wind pipe) of dogs in connection with surgical procedures. The person who performed the surgical procedures noted that when using the treated tubes there was less coughing and chewing on the endotracheal tubes than when conventional tubes were used in similar procedures, and also noted that the animals remained asleep with lower concentrations of general anesthetic agent. None of the animals suffered from any sequela that could be noted.

EXAMPLE 3

Ninety five grams of pellets of vinyl-urethane copolymer (Vythene, Dexter Chemical) and 5 grams of dibucaine base were baked at 93 deg C. for 12 hours with occasional stirring. This process incorporated the dibucaine base into the material of the pellets. Three grams of these treated pellets were further treated by pressing between two metal plates held at 171 degrees C. in vacuum to create a sheet of film about 0.25 mm thick. A sheet of film emerged that was clear, elastic, and very strong. It is believed that the pressing operation simulates the mixing and working of such pellets when they are extruded in a conventional processing for making intubation devices. A piece of this film was tested on the tongue and lips and found to have strong anesthetizing properties. Numbness started to develop in 5 minutes, peaked in intensity in 15 minutes, and persisted for at least 45 minutes. A piece of the film was soaked in 38 degree C. water for 24 hours. It is believed that this soaking procedure simulates the exposure of a tube to aqueous fluids during emplacement in a body passage. At the end of the soaking period the film was again tested on the tongue and lips and exhibited anesthetizing effects as before, but with a slower onset and somewhat diminished intensity.

EXAMPLE 4

Ten grams of lidocaine base and 90 grams of vinyl-urethane copolymer pellets were baked with agitation at 93 degrees C. for 12 hours. At the end of this treatment the pellets stuck firmly to one another. After cooling, the pellets were broken apart, and 3 grams were pressed at 171 degrees C. into a film about 0.25 mm thick. The film was clear, elastic, and tough. When a piece of this film was held on the tongue, intense numbness developed after 5 minutes and persisted for at least 15 minutes. After soaking the film in 38 degree C. water for 24 hours, a test against the tongue showed a numbing effect but at a diminished level. Two hours after the soaking, the film again had strong numbing properties.

EXAMPLE 5

A solution of 30% lidocaine base in ethyl acetate was prepared. A #14 naso-gastric tube made of polyvinyl chloride was coated by dipping in this solution. The coated tube was then baked for 12 hours at 77 degrees C. to drive off the ethyl acetate and incorporate the lidocaine base into the tube material. The tube was then passed into a subject's stomach through the nose (with substantial discomfort because of the marked sensitivity of the nose plus problems with the gag reflex). Initially after introduction of the tube, any movement of the tube caused sharp pain in the nasal passage and induced gagging. After a few minutes had passed, the tube could be manipulated without causing gagging or discomfort. The tube was taped in place, left for 12 hours, and removed without disturbing sensations. When tested later on the tongue and lips, numbing effect was still present, although in lowered intensity.

In the foregoing examples, whereas novel, desirable effects were demonstrated in useful form, it was found that the products, if not used quickly, became tacky to the touch over time, and, for some purposes, were not of acceptable quality or stiffness. The starting polymer pellets or tubes in each case contained usual quantities of plasticizer, as is common in making vinyl products and the like.

It has been further discovered that the anesthetic base has an unexpectedly strong plasticizing effect which combined with the already-present plasticizers in conventional wall materials, can constitute an over-load of plasticizer. This can produce, over time, objectionable surface tackiness and undesirable flexibility. It has been found, however, that by considering the anesthetic base as a plasticizer and by then reducing the total plasticizer content to conventional proportions taking the anesthetic base itself into account as a plasticizer, a product can be produced with predetermined desired flexibility, less tackiness to the touch and with significantly improved shelf life. This discovery has led to products with significantly improved commercial features.

EXAMPLE 6

In an experiment to demonstrate the plasticizing effect of a local anesthetic in base form, vinyl film was pressed effectively with 40% lidocaine base and 60% non-plasticized polyvinyl chloride without addition of any other plasticizer. At a relatively low temperature, about 165°–200° F., the local anesthetic base was imbibed into the polyvinyl chloride powder. Subsequently, the powder in which the lidocaine had been imbibed, was pressed at 325° F. for four minutes. The powder was transformed into a thin, continuous clear, very flexible film that has anesthetic properties, the lidocaine base being dissolved in the vinyl film.

EXAMPLE 7

In an analogous way, a product may be extruded. The general process employed is illustrated in FIG. 11. In a specific embodiment a non-plasticized vinyl powder is treated at the same low temperature as described in Example 6 to imbibe the lidocaine base, followed by the passage of the treated powder through an extruder to extrude it to form extruder-feed pellets. The pellets, with lidocaine now imbibed, is then used as a feed material in various forming processes, e.g. extruding vinyl tubing in the conventional way, or extruding an outer- or inner-anesthetizing layer in a co-extruded product, or forming an extruded tubular preform from which a balloon or cuff is blown or producing and applying a liquid or molten coating material upon a preformed object.

EXAMPLE 8

The observation has been made that when one uses lidocaine as the only plasticizer for polyvinyl tube at relatively reduced concentrations as may be desired in view e.g. of economics concerns, the lidocaine is not delivered to the tissue as rapidly as may be desired under some circumstances. It has been found, however, that improved performance is achieved when the anesthetic base is combined with another plasticizer, which may even be another anesthetic base, prilocaine. Thus, while one can make an effective product using e.g. 10–20% lidocaine in the absence of other plasticizers, where improved mobility of the anesthetic base is desired, it is preferred that there be present an additional plasticizer, e.g., prilocaine or IDOP (diiso-octyl phthalate) or another such conventional plasticizer or combination of plasticizers, such as ESO or adipic acid. Preferably the additional plasticizer constitutes at least about 25% of the plasticizer present, by weight, and most preferably about 50% of the total percentage of plasticizer present, though it may be greater. At least 25% of the total plasticizer by weight is preferably local anesthetic base, and as indicated, for certain applications most preferably about 50% by weight.

Particularly good results for endotracheal tubes are obtained by incorporating IDOP as the additional plasticizer. A very satisfactory ratio of total plasticizer was found to be 50% lidocaine base, 50% IDOP ] by weight, and employing 40 parts by weight of the combined plasticizer to 60 parts by weight polyvinyl chloride, for making a thin film having flexibility of a character useful for the inflatable cuffs of endotracheal tubes, e.g. cuff 21 of the endotracheal tube of FIG. 2.

A specific composition is in parts by weight, 100 PVC, 10 IDOP, 3 heat stabilizer, ¼ stearic acid, and 32.5 lidocaine (about 12.5% of the total weight) to produce a balloon film material of 70 durometer, suitable for use as a low pressure inflatable endotracheal cuff, with rapid anesthetic onset. For a composition of less rapid onset, the major ingredients may be present in percentages by weight, as follows: 60% PVC, 30% IDOP, and 10% lidocaine. The total composition in parts by weight may for instance be PVC 100, IDOP 30, ESO 5, stabilizer 5, and lidocaine 20, to achieve 85 durometer.

For making the shaft 20 of the endotracheal tube shown in FIG. 2, a somewhat harder composition is desired. This is attained by incorporating 10% lidocaine and 20% IDOP, by weight, with 70% polyvinylchloride.

The hardness or softness of the resulting product depends not so much on the ratio of the local anesthetic plasticizer to the other plasticizer as much as it depends on the total quantity of plasticizer present.

Since the part of the endotracheal tube that comes in intimate contact with the trachea and thus traumatizes the trachea is the flexible, inflatable cuff 21, a greater percentage of the anesthetic in certain cases is preferably used in the cuff substance to achieve a greater anesthetizing effect, while less is used in tubular shafts for reasons of economics.

EXAMPLE 9

Prilocaine base was produced by reaction of the hydrochloride form of prilocaine with sodium hydrate, to produce at Ph 11 a liquid form of the anesthetic base at room temperature. Polyvinyl chloride powder is heated to 185° F. and the prilocaine base is imbibed into solution in the polymer powder. The imbibed resin is then introduced to a pellet-forming extruder. In some examples, additional plasticizer is added and in other examples not, e.g. concentration of 30% lidocaine alone are employed. Extruder feed pellets are thereby formed. Using such pellets as feed, thin wall balloon preform tubing is extruded. Thereafter a local mid portion of a section of the preform is heated under controlled conditions and the section is introduced to a blow mold. Gas pressure is applied to blow the heated section into the form of a balloon. Inflatable balloons of the form of floppy endotracheal cuffs and of the shape of balloons for Foley catheters are effectively formed. The film of the balloons is soft and supple and is found to have lasting topical anesthetizing qualities.

EXAMPLE 10

A general process by which the anesthetic base is applied as a step following formation of an article is illustrated in FIG. 12.

In a preferred embodiment, an endotracheal tube cuff of pvc is formed using standard techniques except that less plasticizer is employed from that required to meet the predetermined desired flexibility (durometer) requirements for the finished product. A controlled thickness of liquid prilocaine base is applied to the exterior of the temporarily distended cuff while the cuff is moderately heated to e.g. to 165° F. to expedite diffusion of the anesthetic base into solution in the cuff material. The thus-applied anesthetic base then serves as additional plasticizer to decrease the durometer of the film to the desired predetermined value. After the coated layer has dissolved into the cuff material the cuff is applied by conventional techniques to the shaft of an endotracheal tube.

Following the same techniques other self-anesthetizing medical balloons are formed including the balloons of Foley catheters.

The resultant product produces rapid onset of topical anesthesia.

EXAMPLE 11

Endotracheal tubes made as described in examples 8, 9 and 10 are useful during surgical procedures where it is critical that the patient not cough but remain exceedingly still. An example is opthamological surgery. Any coughing during anesthesia for such a procedure is critical because if coughing occurs, the vitreous humor of the eye can be displaced.

During such an operation, it is desirable to have the anesthetizing effect of the local anesthetic delivered from the device begin at least within about 5 minutes of intubation because muscle relaxants administered before introduction of the tube into the trachea usually last five to 10 minutes before beginning to wane. After that, it is important that the patient not react to the presence of the endotracheal tube.

Endotracheal tubes made according to the present invention do not cause reaction as long as the patient is in a reasonable general anesthetic state. Under these conditions the patient is found not to cough on the tube.

Presently preferred compositions for use in conditions where it is desired to have onset of the anesthetic effect occur within five minutes and taking advantage of the plasticizing effect of lidocaine are described in Examples 8, 9 and 10. Another effective device for eye surgery includes a salt form of the anesthetic, e.g. lidocaine hydrochloride, present at the immediate surface of the device, as a result of conversion of the dissolved base form anesthetic, as described later herein.

EXAMPLE 12

The invention is also useful in virtually all other surgical procedures involving endotracheal tubes. Near the end of a procedure when the anesthesiologist begins tapering off the amount of anesthesia administered to the patient and the muscle relaxants have worn off, it is a particular advantage if the attending physician is able to adjust the position or remove the endotracheal tube without causing coughing or bucking of the patient. Coughing or bucking, for instance, following procedures such as hernia repair, are likely to cause rupture of the stitches. Effective local anesthesia under these conditions is maintained by endotracheal tubes and cuffs according to this invention.

Also, it has been observed that with endotracheal cuffs and tubes containing lidocaine in solution, as have been described, persistence of numbness on the tongue lasts for only about 10 minutes after the film or tube containing the lidocaine local anesthetic has been removed. This indicates that similar numbness should persist only for this time in other tissues of the airway. Such shortness of persistence of anesthesia is desirable as it avoids problems with aspiration of vomitus that might occur due to prolonged effect of anesthesia. Prilocaine is also useful for such applications as its effect also lasts about 10 minutes, whereas some other anesthetics such as dibucaine may be less suitable for this particular application because the anesthetic effect lasts for, e.g., 45 minutes after removal of the tube.

EXAMPLE 13

For use of endotracheal tubes for patients whose breathing is supported by a respirator for prolonged periods, there are different considerations.

On a respirator, one may desire the self-anesthetizing endotracheal tube to remain in place for days rather than hours, and the lasting anesthetic effect after removal is less of a consideration. In this case, the shaft 20 of the tube itself is extruded with a large quantity of, lidocaine or dibucaine in its composition, for example, to enhance the long-term effect of the local anesthetic upon the contacted tissue.

A composition of 10% IDOP, ], 10% lidocaine base, and 80% vinyl, produces a tube of suitable characteristics in which the anesthetic effect lasts for one or a few days to keep the tissues numb.

A composition formulated for fast onset during administration of general anesthesia is also useful for applications requiring a longer duration of use. It is contemplated that in some instances, the same tube that is provided for general anesthesia will also be useful for patients on the respirator with resultant simplification of maintaining hospital inventory and permitting economies of bulk purchase. In a preferred embodiment of a tube for such diverse applications, it is presently preferred to employ lidocaine or prilocaine. In another preferred embodiment, the anesthetic at the surface only is of the water soluble salt form, either as a result of separate application or as a result of conversion of the base form that is present in solution near the surface, while deeper lying anesthetic is of the base form, in solution.

EXAMPLE 14

An alternative embodiment useful during surgical anesthesia, where duration of anesthetizing effect is not as important as it is for critical care patients, is illustrated in FIG. 3. The endotracheal tube is provided with a loose fitting thin sleeve 30 (not tightly adherent to the endotracheal tube). The sleeve 30, e.g. of 0.007" thickness, is extruded from the same mixture of local anesthetic, IDOP and resin as is used for the cuff 21 of FIG. 2. In this manner, one avoids the expense of including the anesthetic agent in the entire wall of the shaft of the endotracheal tube while still providing four to five hours of local anesthesia to the airway.

In this particular embodiment in a localized region, the sleeve 30 is blown to form the cuff 21 itself. As shown in FIG. 3, the sleeve 30 is bonded at both ends, 31 and 32, to the shaft 20 of the endotracheal tube, for instance, heat sealed to a vinyl tube. Similarly, in another preferred embodiment, the sleeve at the proximal end of the cuff 21 or balloon is similarly bonded to shaft 20. In use, the separate nature of the sleeve wall prevents substantial diffusion over time of the anesthetic into the vinyl wall of the tracheal tube itself, thus contributing to the shelf life of the product.

Furthermore, the smaller diameter sleeve portion proximal of the balloon as shown in FIG. 3 in use is distended by the low pressure inflation air, to provide a cushioning, protective effect to tissue and structures engaged by the endotracheal tube and ensuring good tissue contact for transfer of the anesthetic.

EXAMPLE 15

The invention has wide applicability to other types of medical tubes. One that has been tested and found to be effective is prolonged intubation of the stomach through the nose with a self-anesthetizing naso-gastric tube for keeping the stomach drained of fluids. The points of pain for a naso-gastric tube are primarily in the nose. These points may not hurt initially, but within a day or so, the nose becomes very irritated, sore and painful. Pain also develops in the back of the throat since the tube is a foreign body that causes the patient to reflexively swallow in attempt to dislodge the foreign body. Pain arising at these points can readily be alleviated according to the invention.

A conventional pre-formed naso-gastric tube dipped in the lidocaine base and ethyl acetate has been found to emerge very soft, easily kinked and somewhat difficult to insert. By reducing the amount of other plasticizer incorporated during manufacture of the tube, this detrimental result can be avoided. Thus, one starts with a stiffer, harder durometer tube prior to dipping.

Thus, a pre-formed vinyl tube formed with reduced amounts of conventional plasticizer is treated by dipping in a 25% solution of lidocaine base and ethyl acetate, following the procedure of Example 5. The patient will remain comfortable with the tube in his nose for approximately six days. In lieu of dipping, these tubes can be extruded directly using the formulation that has been described in which the anesthetic base serves as predetermined plasticizer of the vinyl resin.

EXAMPLE 16

Another application of the invention is a chest tube or other drainage tube in the body that extends through a sensitive area. In a specific example the drainage tube of outer diameter in the range of 5/16 inch to ½ inch and wall thickness of 1/16 inch has a length of 2 feet. In the distal-most 4 to 6 inches of length are provided drainage holes. For instance, in the first 4 inches of the tube 6 oval holes, with direction of elongation axially aligned, are spaced along and about this tube. By including lidocaine base in its composition, the tube becomes more readily tolerated.

Figure 6:
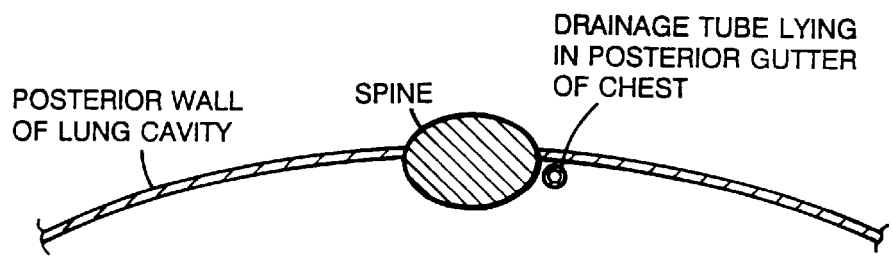
FIG. 6 is a diagrammatic illustration of a drainage tube according to the invention, placed in the posterior gutter along the spine, with its interior surface directed to the lung cavity and its exterior surface directed toward the posterior chest wall.
Figure 7:
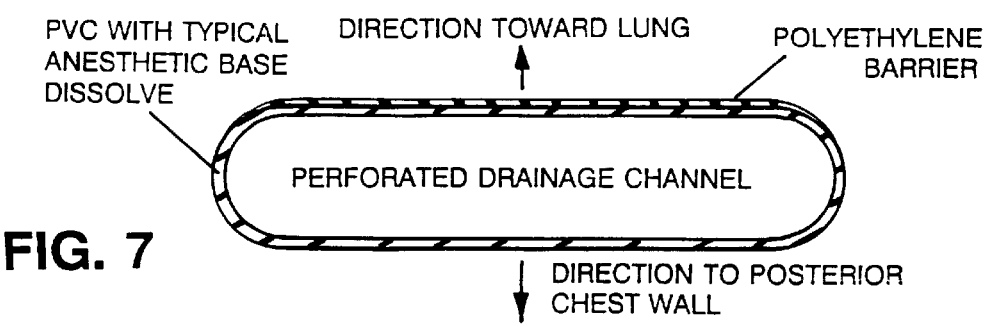
FIG. 7 is a diagrammatic illustration of a preferred flattened form of the chest tube with a barrier layer directed toward the lung cavity.

An improved chest drainage tube is shown in FIG. 6. In a thoracotomy, an opening in the chest is created between the ribs, the ribs being spread apart, through which an operative procedure is performed, usually upon the lungs. The procedure may be used when cancer of the lungs requires removal of part or all of the lung. During recuperations, these incisions are very painful in the first several days. According to this aspect of the invention, a chest tube with a large amount of local anesthetic dissolved in the tube wall or outer layer of the tube is placed in the posterior gutter of the chest. The tube is fixed next to the intercostal nerves such that topical analgesia is provided to the skin and the chest wall incision, sustained for several days for the patient.

One effect of such a tube is to relieve pain. Another is to enable drainage from the body cavity. Conventionally placed tubes that extend out of the chest wall are very irritating to the patient if moved in any way. The present invention enables patients to better tolerate the tube. The use of such tubes can thus be more frequent, with considerable benefit to patients.

EXAMPLE 17

There are also important embodiments of the invention for urology. Certain urethral catheters are currently made of vinyl. Especially for the male, a catheter that is left in the bladder is very irritating to the penis. A Foley catheter construction according to FIG. 1 or with a sleeve 30 as shown in FIG. 3 made from a composition of lidocaine base and vinyl and the catheter itself also made out of the same composition, can be held in place essentially without discomfort. The anesthetic base serves as at least partial plasticizer to reach the desired flexibility of the urethral tube as described above.

EXAMPLE 18

Local anesthetic bases (lidocaine base in particular) are very soluble in vinyl, and when coated or applied on the surface or into a surface layer of a vinyl tube tend, over time, to migrate into the deeper aspects of the tube, thereby attenuating the effect on the surface of the tube. According to a further aspect of the invention, a compatible, intermediate barrier coating, p.v.a. for example, is provided on the surface of a vinyl tube before the application of a vinyl-lidocaine coating. The p.v.a. coating serves at least as a partial diffusion barrier that prevents substantial migration of lidocaine from the surface of the tube into deeper aspects of the tube, thus enabling restriction of the total amount of lidocaine required to fabricate the tube.

EXAMPLE 19

Another feature which slows migration of local anesthetic bases into deeper aspects of vinyl tubing is accomplished by treating the lidocaine-p.v.c. coated tubing with hydrochloric acid, thereby converting the coating or a superficial portion of it to the water-soluble hydrochloride form which forms a fine precipitate in the tube wall. Since the hydrochloride is insoluble in the vinyl, it remains as a precipitate of fine particles in the treated surface region.

EXAMPLE 20

A medical tube is first formed according to one of the forms of Example 8. Then to provide a superficial distribution of the water-soluble hydrochloride form, for quick onset time, the exterior surface of the tube or cuff is treated for a suitably limited duration with hydrochloric acid vapors to convert the anesthetic base to hydrochloride form, which precipitates in the vinyl in a micro distribution at and near the surface. Such a product can combine fast onset with long duration of effective topical anesthesia.

For a tube or other article in which the salt form of the anesthetic is desired substantially below the surface, advantageously a soluble porsigen (distribution of fine soluble substance that is to be dissolved and washed away) is included in the feed stock from which the anesthetic base-laden article is extruded. Subsequently the article is treated with solvent, e.g. water, to dissolve the porsigen to form a network of pathways into the interior of the resin. The tube is then treated with acid vapor, with the pathways providing access to the acid to cause deeper lying anesthetic to be converted to the salt form. During use the deeper-lying anesthesia salt is then available to be mobilized by body fluids via the pathways.

EXAMPLE 21

Figure 8:
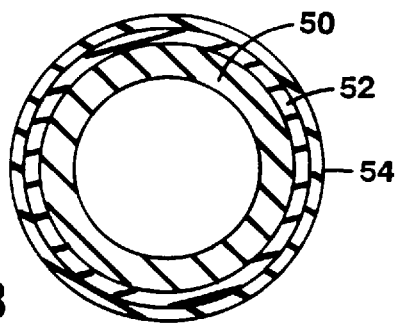
FIG. 8 is a cross-section of a tube formed according to the invention, formed by co-extrusion techniques, and having an exterior surface through which anesthetic is applied.

A tube having an anesthetic-diffusion barrier layer is formed as a coextrusion of the form shown in FIG. 8. The inner layer, constituting main body 50 of the tube, e.g. about 75% to 85% of the entire wall thickness, comprises conventionally plasticized polyvinyl chloride, and its flexibility establishes the main structural properties of the tube. Intermediate co-extrusion layer 52 comprises a compatible polymer in which the topical anesthetic is not as soluble as it is in vinyl. Selected grades of polyethylene, for instance, high density polyethylene may be employed or other polymers or copolymers of known compatibility with p.v.c. which display a slower anesthetic diffusion capability than p.v.c. Depending upon the diffusion barrier qualities of the material selected for the inner layer, or for other properties, e.g., kink resistance or passability, that such layer may be depended upon to contribute to the tube, barrier layer 52 may constitute from about 1% to about 10% or more of the total wall thickness of the coextrusion. Outer, self-anesthetizing layer 54 constituting from, e.g., about 5% to about 25% of the wall thickness, is typically p.v.c. or other resin in which anesthetic base is soluble, and it may contain only the anesthetic base as plasticizer. For example, prilocaine is either imbibed in the starting material, or painted, dipped or sprayed on as a post application process, and allowed to be imbibed and enter into solution in the tube wall. In other embodiments, e.g., in the case of lidocaine, other plasticizers may be present, to contribute to the mobility of the lidocaine, or to contribute desired flexural or other physical properties, to the exterior layer.

In certain embodiments, after fabrication, the exposed outer surface of the tube or other coextruded device may be treated, e.g. with a hydrochloric acid solution, e.g. to precipitate superficial crystals of the hydrochloride form to provide a rapid onset effect as has been described, while depending upon diffusion of the base form for long term sustaining of the topical anesthesia.

EXAMPLE 22

Figure 9:
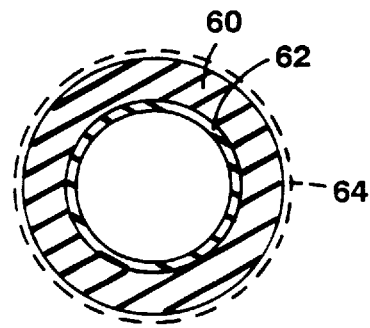
FIG. 9 is a cross-section of a further tube according to the invention in which the internal lumen is protected from dissolved anesthetic with another feature suggested by dashed lines.

The form of coextrusion shown in FIG. 9 is constructed to convey fluids to or in the body, e.g., enteral food mixtures, blood, or drug solution from a subcutaneously implace port. The outer, major thickness layer 60 of the tube comprises e.g., p.v.c. in which the topical anesthetic is in solution according to the previous examples. An internal barrier layer 62 is provided to restrict diffusion of the anesthetic to the contents of the lumen of the tube. Layer 62 may be of selected material and thickness to serve effectively as a total barrier to the migration of the anesthetic. Such construction is useful for a naso gastric or PIG enteral feeding tube to prevent introduction of the anesthetic to the nutrients. It also is useful in a drainage tube to prevent loss of anesthetic to the drainage liquid, thus to enhances the useful life of the product.

The selected material and thickness for internal layer 62 may instead be selected to serve as a metering layer to control the diffusion rate and thus the dosage of the anesthetic being introduced to the contents of the lumen, as in the case where lidocaine is to be introduced to blood or a saline solution for antiarrythmia therapy. Thus inner layer 62 may comprise vinyl in which the anesthetic is not dissolved, but through which it can diffuse at a predetermined rate. In other instances the diffusion rate of the PVC itself is employed as a control to meter the administration of the dissolved baseform anesthetic.

In any case where the selected polymer composition is not an approved material for the duration the tube or device is to be within or exposed to fluids in or entering the body, the internal layer may be selected to have greater biocompatibility than the substance of main body layer 60.

Likewise, as suggested in dashed lines in FIG. 9, an outer coextruded layer 64 may be employed for either instoring or biocompatibility functions (or both) following the above principle. Also, in cases where the function of the tube is to deliver anesthetic to fluid within the lumen, outer layer 64 may be selected to have barrier qualities, to prevent loss or exposure of the anesthetic to surrounding tissues or fluids.

EXAMPLE 23

Figure 10:
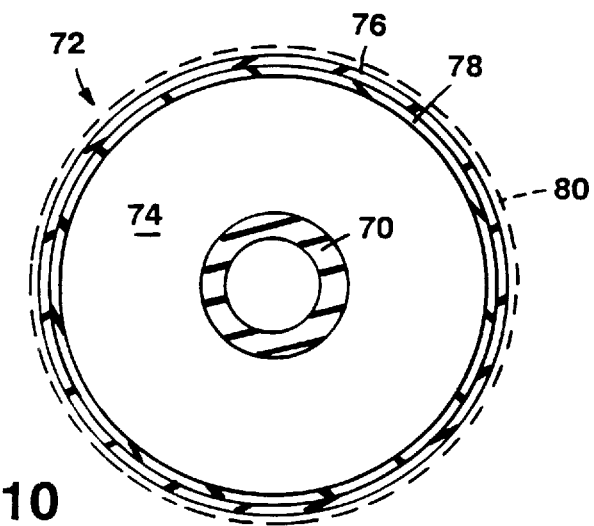
FIG. 10 is a cross-sectional of a further tube having an inflatable member according to the invention.

Referring to FIG. 10, the cross-section represents a cross-section of a balloon catheter or endotracheal tube. Inflatable balloon or cuff 72 is mounted to shaft 70. The balloon or cuff is depicted in inflated state with space 74 filled with inflation fluid which may be air or liquid, depending upon the application. It may also comprise radio-opaque contrast medium for cases of percutaneous insertion and radiographic placement.

The wall thickness of the balloon or cuff 72 is of coextrused form, as a result, e.g. of coextrusion of the preform from which the balloon or cuff is blown.

The outer layer 76 comprises the anesthetic-delivering layer and may comprise, e.g., p.v.c. formed from anesthetic imbibed feed pellets, or as a result of post-application, as by introduction of prilocaine in the liquid state or by application of the anesthetic in a carrier as has been described.

The inner layer 78 may be formed of a selected different material for providing, e.g., desired physical properties to the overall balloon, and/or to minimize the amount of anesthetic by providing barrier properties, e.g. to concentrate the anesthetic in outer regions of the cuff or balloon thickness.

As indicated in dashed lines, outermost layer 80 may also be included, e.g., for instoring or biocompatibility purpose as has been described. It can also carry a topical anesthetic, e.g., to achieve rapid onset. Thus outer layer 80 may include anesthetic in water soluble form. It may also include porsigens or the like, for instance porsigens included in p.v.c., to enable greater mobility of the anesthetic base or the hydrochloride form to the outer area, to enhance the rate of administration.

In one case the material of the inner layer (or one of a multiple number of inner layers) is non-extensible and determines a predetermined maximum diameter of the inflatable member, to serve, e.g., as a dilatation balloon. In one case such a layer is PET. In the case the resin in which the anesthetic is described is not entirely compatible with another layer, an intervening coextruded layer is provided that is compatible with the different resins on its two sides.

OTHER EMBODIMENTS

There are, of course, many other situations in which vinyl drainage tubes are necessary to drain puss and fluid from an abscess or from the abdomen. These tubes can be manufactured to incorporate local anesthetic in their composition following the above examples to enable the patient to be much more comfortable while intubated during the post-operative period.

In post-operative cases, the tube often protrudes through the abdominal wall. Pain is derived from sympathetic innervation of the peritoneal cavity. In addition, pain arises at the skin interface where somatic nerves transmit pain caused by easy movement of the device. PEG and peritoneal drainage tubes can thus be formed that are more tolerable to the patient. These and similar sources of abdominal pain are thus addressed according to the invention.

Similar drainage or drug introduction tubes associated with the head and neck or the vascular system can be constructed according to the invention. For intestinal applications, in addition to the naso-gastric tube, there are situations in which long tubes are used to decompress the bowel. Such tubes pass through the nose and are carried into the bowel to a point of obstruction to carry excretions away. Such intubation is extremely uncomfortable for the patient. Safety of such procedures as well as patient tolerance can be readily improved with the methods and compositions of the present invention.

In some cases the anesthetic base, such as lidocaine, may be dissolved in a biocompatible polymer, or in another polymer covered with a biocompatible polymer, as an implant for timed release of e.g. lidocaine as a long-term antiarrhythmia or antiseizure medication.

In one embodiment, lidocaine base in effective quantities is dissolved in un-plasticized polyvinyl chloride carrier material in a manner adapted for exposure to the body under conditions in which the lidocaine can gradually reach the bloodstream. The blood flow then transports the lidocaine to the site at which the drug is effective, e.g., to block arrhythmia or to serve as an antiseizure agent for epileptic patients.

In another embodiment, propafenone base in effective quantities is dissolved in a resin, and especially a thermoplastic resin in which it is soluble, in a manner adapted for exposure to the body under conditions in which propafenone released from the resin is gradually released into the bloodstream. In one case it is dissolved in orally administratable granules such as coarse or fine powder of thermoplastic resin. The blood flow then transports the released propafenone to the site at which the drug is effective, e.g. reduce, treat, or block arrhythmia. In another embodiment, the resin is formed on or as an implant to release the drug directly to heart tissue or the blood stream. (In the foregoing embodiments lidocaine can be substituted for propafenone.) For demonstration of solubility in resin, propafenone base has been dissolved in a concentration of 50% by weight in intermediate molecular weight polyvinyl chloride, and in concentration of 10% in chlorinated polyethylene. In this and other systems described, when resins are employed in which the solubility of the selected drug is relatively low for the particular therapy desired, a high molecular weight polymer can be selected to provide a higher processing temperature and longer period for the manipulation of the resin and drug in a mill or other processing machine, without degradation or volatilization. These conditions increase the amount of drug that can be dissolved in the resin without degrading the resin, and the relative rigidity of the resin can assist in its grinding to form granular particles or powders.

In one approach the carrier is adapted to provide time release in portions of the body where propafenone base or lidocaine base is exposed to alkaline conditions, for instance in the lower intestine. The carrier may reach the lower intestine by oral administration and passage through the gastric system. For instance it may be coated with a time-dissolvable protective layer that remains in place as the material passes through acidic regions of the gastric system. For this purpose the PVC or other thermoplastic material in which the drug is dissolved may be in the form of orally administered granules in which the propafenone or lidocaine is dissolved, the granules being covered with the time-dissolvable protective coating.

The dissolvable protective coating itself may contain propafenone or lidocaine base which is converted into effective quantities of propafenone or lidocaine chloride during passage through acid regions of the stomach.

In another case, the concentration of the propafenone or lidocaine dissolved in the PVC itself may be greater near the surface of the granules, or otherwise disposed so that some of the propafenone or lidocaine is removed while exposed to acidic conditions, but an effective concentration remains in the granules as the granules reach the lower intestine.

The particular concentrations of propafenone or lidocaine to employ in the resin can be determined once the parameters of the mode of administration have been selected, e.g., selection of the physical form of the delivery carrier and the point and nature of the absorption to be employed, because effective levels of propafenone or lidocaine in the bloodstream for the antiahrrythmia and antiseizure treatments is already known to the medical field.

As indicated above, it has been observed, according to the invention, that numerous drugs are soluble in polyvinyl chloride and chlorinated polyethylene. It has been observed that these drugs have at least one benzene ring, are of base (e.g., free amine or amide) form. They have a lower melting point than the hydrochloric salt form of the drug, that makes them practically processable with thermoplastic resin, e.g. at temperatures in the range of about 250° F. to 350° F., and up to 450° F. for high molecular weight resins.

It has been observed that the drugs can have a plasticizing effect on the resin.

It has been realized that the solubility in resins of drugs of such molecular structure, in a general way, can be predicted from the known properties of plasticizers such as phthalates, glycolates, and citrates which are also characterized by an aromatic ring. Thus it is realized that for the class of drugs having an aromatic ring, and especially a single aromatic ring, it can be reasonably stated that such drugs will have solubilities in the range of thermoplastics in which plasticizers of similar molecular structure have solubility. Phthalates are soluble, e.g. in polymers and copolymers of polyvinylchloride, chlorinated polyethylene, cellulose nitrate, ethyl cellulose, cellulose acetate, polystyrene, polyvinyl butyryl, acrylic resins, alkyl alkylacrylates, acrylonitrile rubbers, and chlorinated rubbers such as neoprene. Drugs having similar structure with a single benzene ring are likewise soluble in these resins, and can be advantageously dissolved in the resins as a step in the preparation of a drug delivery composition.

Of particular consequence is the realization that drugs which have an observable anesthetic characteristic (even if the main use of the drug is not for anesthesia, but for other purposes such as antiarrhythmia or other treatment of the neurophysiological system of the body) can be administered in prolonged manner by systems comprising thermoplastic resin in which the base form of the drug has been dissolved.

In certain resins, certain drugs are found to be highly soluble, and enable the use of relatively low molecular weight resins. For instance polyvinyl chloride with specific viscosity of about 225 (intrinsic viscosity of between about 96 and 99) has been demonstrated to receive in solution as much as 50% of the drugs lidocaine and propafenone. Such resins are preferred when forming tube, sheet-like or fiber material in which considerable flexibility of the tube, sheet or fiber is desired.

For other applications, such as orally administratable granules of fine or coarse powders, it is desired to form an extrusion of the resin with dissolved drug, and then to grind it to form the granules. For this purpose a relatively high molecular weight, rigid resin may be preferred, for ease of grinding. The high molecular weight, long molecules of such resins permit the attainment of higher processing temperatures and longer residence times in the mill or other processing equipment that is employed to dissolve the drug into the resin. This leads to increase in the amount of the drug that can be dissolved. In turn, this leads to a wider practical range of choice of the resin, permitting use of resins which have other desirable properties, such as meeting requirements of regulatory agencies and the like for prolonged use within the body, as well as to attain process, storage, performance, and economic characteristics.

For those therapies in which more that one drug that is soluble in resin can be selected, another criteria for choice of the system to be employed is the fugitive or diffusive character of the drug within the particular resin. This may be estimated based upon the molecular structure of the drug, the shorter and less complicated the molecule, the more fugitive. For any particular desired therapy, trials with the various drugs and resins are readily conducted to enable empirical observation. Final choice of the constituents and relationships based upon observed, reproducible results is then a matter for those of ordinary skill in formulating drug and resin compositions.

The discoveries described above, have led to the realization that the system of the invention has generality beyond drugs that are known to have anesthetic characteristics. Thus, from the similarity of chemical structure and known characteristics of drugs and resins, it is realized that a wide range of drugs having sufficient unsaturated moieties, aromatic or heteroaromatic moieties, or similar structure can be delivered employing the present invention. Among these drugs are atenol, pseudoephedrine, terbutaline, phenylpropanolamine, acetaminophen, ibuprofen, phenacetin and methylphenidate.

Thus the present invention achieves a new mode of drug delivery that can enable administration of drugs thought previously to have insufficient half life for particular therapies, and for delivery, in prolonged fashion, drugs that heretofore have been required to be administered at disadvantageous frequency.

Finally, further aspects of the invention are illustrated in FIGS. 13–21.

In FIG. 13 a fiber 100 of thermoplastic resin is represented on a much enlarged scale. A small section of the fiber is shown in a still more enlarged scale in FIG. 13A in which stippling denotes anesthetic base or other drugs in solution in the resin. Certain fibers of this construction are characterized as having been formed by extrusion and drawing of thermoplastic synthetic resin in which was dissolved a drug having an aromatic ring and which is soluble in the resin. Other fibers of this construction are characterized as having been formed in similar manner, but of thermoplastic resin not containing the drug. Following forming the fiber, either the fiber per se or when formed with other fibers into a fabric, suture, or the like, is exposed to the drug under conditions promoting the drug entering into solution in the body of the fiber. For instance, the drug may be provided in a suitable soaking solution that promotes entry into solution, e.g. in the case of fibers of polyvinyl chloride resin, a 50% lidocaine base in solution with 50% ethyl acetate may be employed.

In FIG. 14 a tiny spinnerette nozzle 101 is diagrammatically illustrated from which a fiber 100 is extruded from feed stock comprising a drug having an aromatic ring dissolved in a thermoplastic resin in which it is soluble. Alternatively the fiber may be formed without the drug being in the extruded resin.

In FIG. 15 a non-woven fabric 102 is formed by the well known spun bonded process employing spinnerettes according to FIG. 14.

In FIG. 16 a non-woven fabric is formed by the spun bonded process employing spinnerettes 101 according to FIG. 14 and additional spinerettes 103 from which hydrophilic fibers are extruded, to form a composite non-woven fabric.

In FIG. 17 is shown a bandage or compress comprised of layers of non-wovens according to FIGS. 13–16.

In FIG. 18 is shown the post-forming treatment of the non-woven 102 of FIG. 15 in which drug at the surface of the fibers is converted to water soluble salt form by immersion in a slightly acid bath followed by drying 120.

Fibers, threads, yarns, continuous films of perforated films or strips of plastic resin which the drug is dissolved may likewise be treated.

In FIG. 19 a suture 130 is shown on greatly enlarged scale formed of filaments according to FIG. 13 that have been subjected to a crimping process to impart knottability to the filaments 100' that comprise the suture.

In FIG. 20 a suture is shown formed of crimped filaments 100' according to FIG. 19 and crimped hydrophilic filaments 107.

In FIG. 21 is illustrated a compress 120 containing topical anesthetic associated with an ointment 122 that serves as a transfer layer for the anesthetic from the compress to a heating surgical site 24.

Preferred embodiments of the compress are an assemblage comprised, at least in part, of thermoplastic resin components in which an anesthetic base is dissolved or in which a drug of similar structure in base form, having healing properties, is dissolved.

The thermoplastic resin containing the dissolved drug serves as a long term reservoir to dispense the drug to the ointment, from which it transfers to the body, preferably contains a strongly ionic compound, e.g. an ionic surfactant, to aid in passage of the drug through the skin. The ointment itself can contain anesthetic in base form, and may advantageously contain an emulsifier to aid where both oily and watery constituents are present. The ointment may contain a mixture of lidocaine hydrochloride and prilocaine base.

Certain embodiments of this aspect of the invention have one or more of the following features.

The compress is formed of a bat of fibers at least some of which are thermoplastic fibers in which the drug is dissolved. The bat of fibers includes hydrophilic fibers. Alternatively the compress is formed of a non-woven fabric of fibers at least some of which are thermoplastic fibers in which the drug is dissolved. The non-woven fabric includes hydrophilic fibers. And in still another alternative, the compress includes a gel or gel-like substance that includes a constituent comprised of thermoplastic in which the drug is dissolved. The constituent may be a film, shredded film, fiber or granules of the thermoplastic in which the drug is dissolved.

In still another embodiment, the compress comprises collagen alginate dressing containing thermoplastic powder granules in which the anesthetic is dissolved.

Numerous other embodiments are possible within the scope of the invention.

What is claimed is:

1. A tissue-numbing anesthetic article comprising anesthetic base having at least one aromatic ring dissolved in substantial quantity in thermo-plastic resin.

2. The composition of claim 1 wherein said thermoplastic resin has a processing temperature between about 250° and 450°.

3. The composition of claim 1 wherein the drug is dissolved in a coating or surface layer.

4. The composition of claim 1 wherein the drug is dissolved in sheet or film of resin.

5. The composition of claim 1 wherein the drug is dissolved in fibers of resin.

6. The composition of claim 1 wherein the drug has a single benzene ring.

7. The composition of claim 1 wherein the drug of base form is dissolved in a resin in which phthalates, glycolates, or citrates are soluble.

8. The composition of claim 1 wherein said resin comprises a polymer or copolymer of resin selected from the group consisting of polyvinyl chloride, chlorinated polyethylene, cellulose nitrate, ethyl cellulose, cellulose acetate, polystyrene, polyvinyl butyryl, acrylic resins, alkyl alkylacrylate resins (e.g., methyl methacrylate, ethyl ethacrylate, or other lower alkyl acrylates), acrylonitrile rubbers, and chlorinated rubbers (e.g., neoprene).

9. The composition of claim 1 wherein the composition is constructed to reside for prolonged periods in contact with tissue or body fluid.

10. The composition of claim 1 wherein the resin is formed to lie adjacent a surgical or trauma site to administer anesthetic or other medication to the site.

11. The composition of claim 10 wherein the resin is in the form of a thin, flexible wall or fiber of polymeric resin exposed to contact tissue.

12. The composition of claim 1 wherein the resin is configured to deliver local or topical anesthetic in the region of an incision or wound.

13. A wound or incision-treatment device formed to reside at a surgical site, and formed at least in part of thermoplastic resin in which at least a topical anesthetic or other drug is dissolved, the topical anesthetic or other drug having at least one aromatic ring.

14. A wound or incision-treatment device according to claim 13 wherein the device includes said anesthetic or other drug in base form dissolved in resin and in water soluble salt form associated with the resin.

15. A wound or incision-treatment device according to claim 14 wherein the salt form is a hydrochloride salt.

16. A wound or incision-treatment device according to claim 13 wherein the device includes hydrophilic resin in which the base form is dissolved and in which the salt form is imbibed in aqueous solution or in which the salt form resides as crystals as a result of imbibing and drying.

17. A wound or incision-treatment device according to claim 13 wherein the device is a film having a surface that contacts tissue to be treated.

18. A wound or incision-treatment device according to claim 13 wherein the device is a compress or bandage.

19. A wound or incision-treatment device according to claim 13 wherein the device is formed at least in part of thermoplastic fibers in which the drug is present.

20. A wound or incision-treatment device according to claim 19 wherein the device is a suture formed at least in part of thermoplastic resin in which the drug is dissolved.

21. A wound or incision-treatment device according to claim 18 wherein the fibers are at least part of a textile material.

22. A wound or incision-treatment device according to claim 18 wherein the fibers are hydrophobic.

23. A wound or incision-treatment device according to claim 22 wherein the hydrophobic fibers are combined with hydrophilic fibers capable of containing an aqueous substance that promotes release and transport of the drug from the hydrophobic resin.

24. A wound or incision-treatment device according to claim 13 wherein the device is combined with a fluid or ointment that promotes transport of the drug from the resin.

25. A wound or incision-treatment device according to claim 24 wherein the fluid or ointment contains a drug, and the drug from the resin is effective to replenish the drug in the fluid or ointment.

26. A wound or incision-treatment device according to claim 24 wherein the drug in the fluid or ointment and the drug dissolved in the resin include topical anesthetic.

27. A wound or incision-treatment device according to claim 24 wherein the fluid or ointment includes an ionic surfactant that promotes diffusion of the drug through tissue.

28. A wound or incision-treatment device according to claim 24 wherein the fluid or ointment includes a thickener or an ionic exchange additive.

29. A wound or incision-treatment device according to claim 24 wherein the fluid or ointment includes carboxypoly methylene.

30. A wound or incision-treatment device according to claim 24 wherein the fluid or ointment that cooperates with the drug dissolved in the resin includes a combination of topical anesthetics and an emulsifier such as a fatty acid ester.

31. A wound or incision-treatment device according to claim 30 wherein the combined anesthetics in the fluid or ointment are prilocaine and lidocaine.

32. A wound or incision-treatment device comprising fibers of hydrophobic resin in which a drug having an aromatic ring is dissolved.

33. A wound or incision-treatment device according to claim 32 comprising fibers of hydrophobic resin and fibers of hydrophilic resin.

34. A wound or incision-treatment device according to claim 33 comprising the fibers of both types of resin carry a drug.

35. A tissue-numbing anesthetic article comprising a clear layer at least part of which comprises polymeric substance having dissolved therein a topical anesthetic compound, the topical anesthetic compound being more soluble in the polymeric substance than in water, the concentration of anesthetic compound in the polymeric substance being such that when the article is emplaced in contact with tissue, anesthetic compound diffuses to the tissue in contact with the article at a rate to be effective in maintaining anesthesia.

36. The article of claim 35 in which the topical anesthetic compound is base.

37. The anesthetic article of claim 35 in which the resin consists essentially of plasticizable hydrophobic resin.

38. The anesthetic article of claim 35 comprising a film.

39. A tissue-numbing anesthetic article at least part of which comprises polymeric substance having dissolved therein a topical anesthetic compound, the topical anesthetic compound being more soluble in the polymeric substance than in water, the concentration of anesthetic compound in the polymeric substance being such that when the article is emplaced in contact with tissue, anesthetic compound diffuses to the tissue in contact with the article at a rate to be effective in maintaining anesthesia.

40. The anesthetic article of claim 39 in which the polymeric substance is a thermo-plastic resin.

41. The article of claim 40 wherein the resin is polyvinyl chloride or its copolymer.

42. The article of claim 39 wherein the resin is a lower alkyl acrylate or its copolymer.

43. The article of claim 39 in which the anesthetic compound has a single benzene ring.

44. The article of claim 39 in the form of a sheet or film.

* * * * *

UNITED STATES PATENT AND TRADEMARK OFFICE
CERTIFICATE OF CORRECTION

PATENT NO. : 5,810,786
DATED : September 22, 1998
INVENTOR(S) : Richard R. Jackson, et al.

It is certified that error appears in the above-identified patent and that said Letters Patent is hereby corrected as shown below:

ON THE TITLE PAGE:

In Item [57], line 26, delete "an ionic".

Column 3, line 21, delete "an ionic"

Column 5, line 42, delete "in".

Column 23, line 66, delete "a strongly ionic compound", e.g. an ionic".

Signed and Sealed this

Twenty-third Day of March, 1999

Attest:

Q. TODD DICKINSON

*Attesting Officer*     *Acting Commissioner of Patents and Trademarks*